United States Patent [19]

Hanson

[11] Patent Number: 5,586,882
[45] Date of Patent: Dec. 24, 1996

[54] SELF-LIGATING ORTHODONTIC BRACKETS

[76] Inventor: G. Herbert Hanson, 57 Augusta Street, Hamilton, Ontario, Canada, L8N 1P8

[21] Appl. No.: 274,077
[22] Filed: Jul. 12, 1994
[51] Int. Cl.⁶ ........................................... A61C 3/00
[52] U.S. Cl. ..................................... 433/13; 433/14
[58] Field of Search ........................... 433/8, 9, 10, 11, 433/12, 13, 14

[56] References Cited

U.S. PATENT DOCUMENTS

| | | | |
|---|---|---|---|
| 3,772,787 | 11/1973 | Hanson | 433/14 |
| 4,248,588 | 2/1981 | Hanson | 433/11 |
| 4,492,573 | 1/1985 | Hanson | 433/14 X |
| 4,698,017 | 10/1987 | Hanson | 433/13 X |
| 5,190,546 | 3/1993 | Jervis | 606/78 |
| 5,380,197 | 1/1995 | Hanson | 433/8 X |
| 5,474,445 | 12/1995 | Voudouris | 433/11 X |

OTHER PUBLICATIONS

American Journal of Orthodontics and Dentofacial Orthopedics vol. 90, No. 1, Jul. 1986.

Primary Examiner—Nicholas D. Lucchesi
Attorney, Agent, or Firm—Rogers & Scott

[57] ABSTRACT

Self-ligating orthodontic brackets comprise a spring ligating member of U-shape with converging arms movable on the bracket body between slot open and closed positions; in the latter position the spring retains an arch wire in the slot and urges the bracket and wire to their optimum relative positions. The ligating member is of a superelastic shape recovery metal alloy, preferably of thickness from 0.20 mm (0.008 in) to 0.25 mm (0.010 in), with rounded edges. At least the lingual portion of the member to be stiffer than the remainder; at least a part of the occlusal portion can also be stiffer. Alternatively, or in addition, the bracket body has a large mesial distal extending bore between and spaced from the bracket occlusal, lingual and labial surfaces and the arch wire slot occlusal surface. The large bore accepts attachment members used for attachment of a range of auxiliaries, such as hooks and traction springs. Alternatively, or in addition, the arch wire slot gingival wall comprises an additional spring; this can be of shape memory alloy and preset to become effective when heated above its transformation temperature. Alternatively, or in addition the arch wire slot has the lingual and gingival surfaces meeting at an angle from 120 to 150 degrees to provide a larger slot; the slot gingival surface may also be provided by an additional spring member.

30 Claims, 5 Drawing Sheets

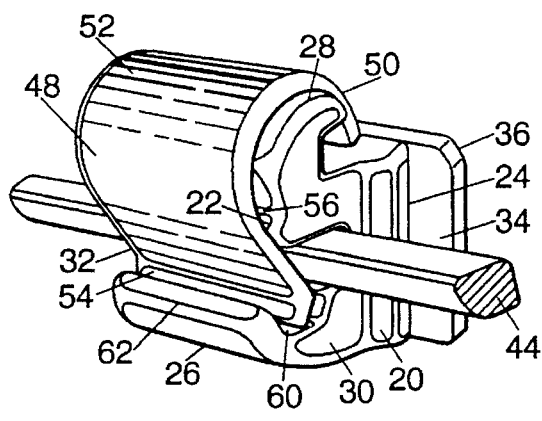

SELF-LIGATING ORTHODONTIC BRACKETS

FIELD OF THE INVENTION

This invention is concerned with improvements in self-ligating orthodontic brackets, namely orthodontic brackets which comprise ligating spring means as an integral part thereof.

REVIEW OF THE PRIOR ART

The majority of orthodontic procedures employ a plurality of brackets that are attached to respective teeth, usually by cementing them to the teeth, together with one or more arch wires, so called because they are preformed to an optimum arch shape corresponding to the desired conformation of the teeth at the conclusion of the procedure. The arch wires are used one at a time, the selected arch wire being engaged in cooperating mesial distal extending slots in the brackets, usually of rectangular cross section, and attached to the brackets by a ligating means of some kind. When these procedures were first introduced the ligating means usually were metal wires that were twisted about the bracket and the arch wire; subsequently as elastomeric materials were developed that could withstand the hostile environment of the human mouth elastomeric loops have become increasingly commonly used. In another line of development each bracket comprises an integral self-ligating spring member; specific examples of such brackets are those disclosed and claimed in my U.S. Pat. Nos. 3,772,787; 4,248,588 and 4,492,573, the disclosures of which are incorporated herein by this reference. These brackets are currently in use in the Hanson SPEED System (Trade Mark) and have proven to be very successful.

SUMMARY OF THE INVENTION

It is a principal object of the invention to provide new self-ligating brackets.

It is another principal object to provide new self-ligating brackets that can be used in combination with other ligating means in circumstances that such additional ligating means may be required.

It is a further object to provide new self-ligating brackets adapted for use with additional orthodontic elements that can be attached to the brackets.

It is a still further object to provide new self-ligating brackets comprising an additional spring also engagable with the arch wire and cooperating with the principal ligating spring.

Orthodontic brackets of the invention comprise:

a bracket body having labial, lingual, gingival, occlusal, mesial and distal surface portions, the body having a mesial distal extending arch wire slot opening to the labial surface portion; and a generally U-shaped ligating spring member of thin resilient material having labial and lingual portions in embracing sliding engagement with corresponding labial and lingual surface portions of the body, the ligating spring member being movable on the body between two positions in which the slot labial opening is respectively open and closed.

In accordance with the invention the ligating spring member is of a superelastic shape recovery metal alloy. Preferably, the thickness of the member is from 0.20 mm (0.008 in) to 0.25 mm (0.010 in). The edges of the member may be rounded to a respective radius of from 0.10 mm (0.004 in) to 0.125 mm (0.005 in). At least the lingual portion of the ligating spring member may be of greater stiffness than the remainder of the member, and in addition at least a part of the occlusal portion may be of greater stiffness than the remainder of the member.

Also in accordance with the invention the arch wire slot gingival surface portion is provided by an additional spring member having its lingual end retained by the bracket body and having its labial end free to move gingivally by engagement with an arch wire in the slot. The additional spring member may be of superelastic shape recovery metal alloy, in which case it may be of preset shape such that the slot lingual and gingival surface portions meet at a common junction at an angle to one another of more than 90 degrees, the member being pretreated so that upon heating above a transition temperature its preset shape is changed to a memory shape with which the lingual and gingival surface portions meet at a common junction at an angle of 90 degrees.

Further in accordance with the invention the bracket also comprises a mesial distal extending bore disposed between and spaced from the bracket occlusal, lingual and labial surface portions and the arch wire slot occlusal surface portion. The bore may be of diameter in the range 0.7 mm–0.9 mm (0.027 in–0.035 in). Such a bracket may be used in combination with an attachment member insertable in the mesial distal extending bore and retainable therein against at least movement in the mesial distal direction, and if required also against rotation about a mesial distal axis. The bore may be of non-circular transverse cross section, the attachment member being of corresponding non-circular transverse cross section to prevent such rotation; alternatively the bore has a radially extending groove in its wall and the attachment member has a cooperating radial projection that engages in the groove to prevent such rotation. The attachment member may be attached to one end of an orthodontic element, such as a traction spring member, and the element may be of transverse dimension small enough for it to pass through the bores of adjacent brackets. Alternatively the attachment member has at one end a hook member for reception and retention of a ligature member. The bracket may also comprise a mesial distal extending slot disposed at the junction of the bracket body gingival and lingual surface portions and opening to the bracket body gingival surface portion, or to the lingual-gingival surface portions jointly.

Further in accordance with the invention in a bracket wherein the arch wire slot has lingual, gingival and occlusal surface portions, and wherein the lingual and occlusal surface portions meet at a common junction at least approximately at a right angle to one another, the lingual and gingival surface portions may meet at a common junction at a greater angle to one another of from 120 to 150 degrees, preferably 135 degrees.

DESCRIPTION OF THE DRAWINGS

Particular preferred embodiments of the invention will now be described, by way of example, with reference to the accompanying diagrammatic drawings, wherein:

FIG. 1 is a perspective view from the labial of a bracket which is a first embodiment, shown with an arch wire in the slot and the ligating spring member in the slot closed position;

FIG. 2 is a similar view of the bracket of FIG. 1 with the arch wire removed and the ligating spring member in the slot open position;

FIGS. 3 and 4 are side elevations respectively of a prior art stainless steel ligating member, and a superelastic shape recovery metal alloy ligating member of the invention;

FIGS. 5 and 6 are cross sections through the spring members of FIGS. 3 and 4, taken respectively on the lines 5—5 and 6—6 therein;

DESCRIPTION OF THE PREFERRED EMBODIMENTS

Figure 7:
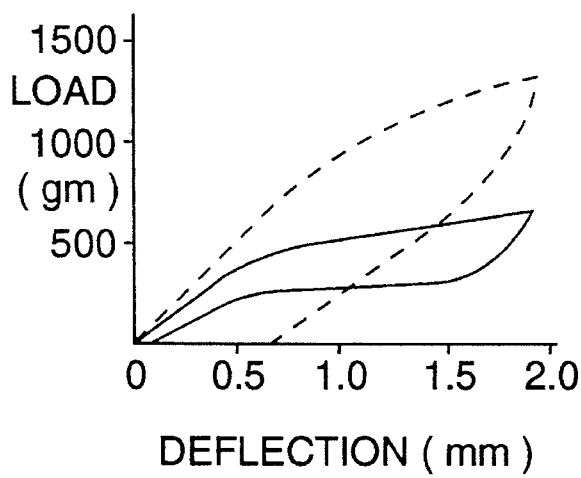
FIG. 7 is a load-deflection diagram comparing a typical characteristic for a stainless steel with a typical characteristic for a nickel-titanium shape memory alloy.

For convenience and simplicity in description the embodiments are illustrated and described herein and claimed in the appended claims as they would be used in the lower central incisor region of a patient's mouth and in the conventional so-called labial technique, in which the brackets are attached to the labial surfaces of the teeth. The brackets of the invention are equally usable in the so-called lingual technique, in which they are attached to the teeth lingual surfaces so that they are concealed from view as much as possible. Again for convenience in description the brackets are described as having specific named surfaces but, as is well known to those skilled in this art, it is usual in their manufacture to avoid sharp edge junctions between the various surfaces, and they therefore usually merge smoothly with one another without a definite junction between them being apparent.

Each bracket of the present invention consists of a bracket body 20 having labial, lingual, gingival, occlusal, mesial and distal surfaces 22, 24, 26, 28, 30 and 32 respectively. Such a bracket is mounted on the respective tooth (not shown), either by the older method of attaching it to a tooth-embracing band, or by cementing it directly to the tooth. When the bracket is to be attached by cement the body lingual surface 24 has a cementing pad 34 attached thereto, which in turn provides a lingual surface 36 that is applied to the tooth labial surface. This pad forms no part of the present invention and it is omitted from many of the Figures of the drawings.

The embodiment of FIGS. 1 and 2 is provided with a rectangular gingival-occlusal transverse cross section, mesial-distal extending arch wire slot opening to the labial surface 22 and having lingual, gingival and occlusal surfaces 38, 40 and 42 respectively. The slot receives an arch wire 44, which usually in the early stages of a procedure is of circular cross section, and which subsequently is replaced by one of rectangular cross section for final control of tipping of the teeth into position. The arch wire illustrated is that more particularly described and claimed in my prior U.S. Pat. No. 4,386,909, the disclosure of which is incorporated herein by this reference. The wire is of partial rectangular cross-section, having its gingival and occlusal surfaces parallel and at right angles to its lingual surface; the occlusal surface is wider than the gingival surface and the labial surface between them is of smooth convex shape. As with any rectangular cross section wire its gingival occlusal thickness is such that it fits in the slot easily but without excessive play.

Means for retaining the arch wire in the slot, and for pressing it lingually into engagement with the slot lingual face, comprise a self-ligating spring member 46 of thin flat springy metal, and of U-shape with converging arms, referred to herein as generally U-shaped, the shape enabling it to embrace the body 20 and to conform closely to the labial, occlusal and lingual faces thereof while in the slot closed position illustrated in FIG. 1. For convenience in description this ligating retaining member may be regarded as comprising opposed labial and lingual portions 48 and 50 respectively, each in embracing sliding engagement with the respective bracket body surface, and a connecting occlusal portion 52. The member is movable with this sliding and embracing movement on the body between the slot closed position shown in FIG. 1 and the slot open position shown in FIG. 2; in the latter position angled edge part 54 of the labial portion 48 engages on a parking land, constituted by a step 56 in the body labial surface, to retain the member in that position.

The lingual portion 50 moves freely without play in a groove formed in the lingual face of the bracket body, the groove lingual side being closed to form an enclosing passage by the cementing pad 34; the portion 50 is relatively straight so as to guide the ligating member for corresponding straight gingival occlusal movement between the two end positions, and is dimpled at 58 at its free end to prevent the member being moved beyond the slot open position off the bracket. When in operative position the occlusal portion 52 is approximately semi-circular, while the immediately adjacent part of the labial portion 48 is concave toward the body in conforming closely thereto. The remaining part of the labial portion that terminates in the edge part 54 is relatively straight for most of its length, while the edge part itself is bent or inclined toward the labial. The bracket body is also provided labially of the arch wire slot with a mesial-distal extending slot 60 having an occlusal opening in the plane of the gingival surface of the arch wire slot and into which the labial end 54 of the retainer spring can intrude, the part of the body forming the slot 60 thereby providing a retaining wall 62 that can be engaged by the ligating member end 54 when the member is in the slot closed position and the wire in the slot is protruding labially out of it. The labial lingual dimension of this slot is such that the retaining wall restricts any such labial movement of the ligating member to the maximum that is possible without overstressing and damaging it.

The bracket is provided with an additional mesial distal extending slot 64, also of rectangular gingival occlusal transverse cross section, at the junction of the bracket occlusal and lingual surface portions, the slot opening to the lingual surface portion. In the event that at the start of a procedure the arch wire is so far displaced from the slot that it cannot be engaged therein, or it protrudes so far out of the slot that the ligating member cannot be moved to the slot closed position, a tie wire or an elastomeric thread can be passed through this slot 64 to secure the arch wire to the bracket until sufficient correction has taken place for the wire to be inserted in the slot and the ligating member closed thereon.

The brackets of the invention are employed in a technique with which each bracket is attached to its respective tooth in an attitude such that, as each arch wire attempts to return to its preformed arch shape, each tooth is moved toward its desired optimized position and attitude. To achieve this all of the torque requirements (rotation about a mesial distal axis), angulation requirements (rotation about a labial lingual axis), and first order pre-adjustments, are obtained by suitable shaping of the bracket bases, particularly of their lingual surfaces and variation of their thicknesses, so that all of the labial faces are aligned when the teeth are in their optimum attitude and rotational position.

It is a fundamental objective with orthodontic procedures that they proceed as rapidly as possible, consistent with the avoidance of undesired side effects, particularly damage to the tooth roots and the surrounding tissue. Orthodontic procedures are only possible because the teeth are securely anchored in the bone of the jaw to the extent that they withstand without movement the surprisingly high impact forces to which they normally are subjected, and yet they can be moved in that bone while remaining securely attached by the persistent application of relatively extremely small forces. This movement in the bone takes place by means of a relatively complex process involving special cells which absorb bone at the positive pressure site (Osteoclasts), and deposit bone (Osteoblasts) at the opposite negative pressure site, the process requiring a minimum or threshold amount of force for it to become established. The tissue and bone of the jaw have a generous blood supply and this should be maintained at as normal a level as possible to maintain the cells healthy and active, and thus facilitate this cellular action. An adequate blood supply is also needed to maintain the surrounding supporting tissue in healthy condition. There is therefore a specific predeterminable range of force that should be employed, namely sufficient to ensure the cellular action takes place, while not so large that the blood supply is reduced, and it is found that in practice the force required is comparatively relatively low. It is difficult in practice to give numerical values to these forces, since the application will vary from tooth to tooth in the same mouth, but it is known that they are considerably smaller than those which are encountered in conventional edgewise procedures. High forces do not necessarily result in faster movement of the teeth, and can result in slower movement, because of the resultant restriction of the blood supply and consequent inhibition of the entire process; there is also the increased possibility of damage to or even death of the tissue and permanent resorption of the bone of the jaw. The optimum procedures are therefore those in which light moving couples within a narrow range above the threshold value are applied as persistently as possible.

Among the advantages of self ligating brackets is that the spring ligating member almost always has an effective life equal to that of the procedure, unlike an equivalent elastomeric ligature which may need to be changed monthly, or even more frequently. A more important advantage is the manner in which the ligating member is able to contribute accurately and at all times to the restoring force urging the teeth to their final optimum positions. This is especially important in the final stages of the procedure, since it reduces the number of changes of arch wire required, enabling relatively very stiff arch wires to be used earlier in the procedure without applying excessive force to the brackets and teeth.

One of the problems involved in the practical design of orthodontic brackets is their extremely small size, and typically one of my prior art brackets currently in use has a body that measures 2.7 mm to 3.0 mm (0.108 in to 0.120 in) in gingival occlusal dimension, 2.1 mm to 2.7 mm (0.084 in to 0.108 in) in labial lingual dimension, and 2.7 mm to 3.0 mm (0.108 in to 0.120 in) in its widest mesial distal dimension adjacent to the lingual body surface 24. The body is attached to a cementing base that usually is about 0.25 mm to 0.50 mm (0.010 in to 0.020 in) wider than the body. The spring ligating member 46 is of stainless steel of about $28$–$29 \times 10^6$ psi elastic modulus (which is a measure of its stiffness), and measures 0.125 mm (0.005 in) in thickness and 1.6 mm to 1.8 mm (0.065 in to 0.072 in) in the mesial distal dimension. Although stainless steel of the highest practical modulus is used the spring ligating members are stressed surprisingly close to the elastic limit of the metal as they are moved between slot-open and slot-closed positions, and the amount of displacement required to exceed the elastic limit is relatively small. Once that limit has been exceeded, for example by the operative carelessly moving the member and/or attempting to force the member to close over a stiff arch wire that protrudes too far out of the slot, then it may no longer function successfully as a spring. This may require the bracket to be replaced completely, since it is not usually convenient for the orthodontist to attempt to replace the ligating member "in situs", especially since the mounting of the member on the bracket body brings it so close to the elastic limit. Such replacement is of course inconvenient and unpleasant both for the orthodontist and the patient.

Figure 8:
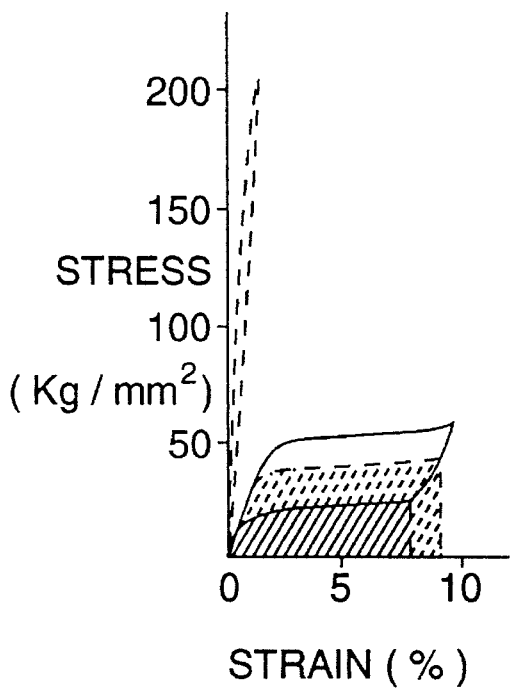
FIG. 8 is a stress-strain diagram comparing a typical characteristic for a stainless steel with a typical characteristic for a nickel-titanium shape memory alloy.
Figure 9:
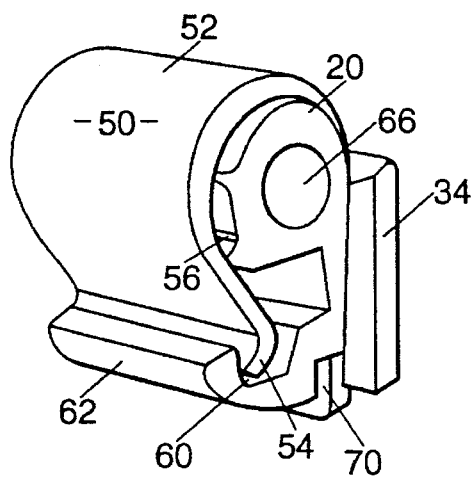
FIG. 9 is a perspective view from the labial of another embodiment provided with a bore enabling the use therewith of additional orthodontic elements, such as attachment members, wire and elastomeric ligatures, traction springs and hooks.

The problem involved is illustrated by FIGS. 7 and 8, which are respectively load-deflection and stress-strain curves in which the characteristics for a typical stainless steel wire are shown in broken lines. Owing to the high modulus the stress-strain characteristic is extremely steep, so that quite small displacements produce large stresses in the wire. Perhaps more importantly the load-deflection curve shows that, for example, if the deflection applied is as much as 2 mm, then the wire takes a permanent "set" of approximately 0.7 mm, which clearly would render the spring ligating member ineffective thereafter.

Various so-called shape recovery metal alloys, also frequently called superelastic metal alloys, have recently been developed which are highly resistant to overstressing and resultant permanent deformation, as compared to stainless steels. The respective "superelastic" load-deflection and stress-strain characteristics of such an alloy are shown respectively in FIGS. 7 and 8 in solid lines, and the very flat shape of these characteristics, as compared with those for stainless steel, will be noted. In particular, it will be noted from FIG. 8 that above a relatively low stress value the application of additional stress causes a considerable increase in strain, while from FIG. 7 if a wire of this material is deflected by as much as 2 mm, unlike the stainless steel wire, it returns to the non-deflected state with virtually no permanent set. Wires and flat springs made of these alloys can be bent to a desired original "memory" shape and set in that shape by suitable heat treatment; subsequently if heated above a transformation temperature they will return to their original shape. The atomic structure which produces this phenomenon also causes these alloys to exhibit the so-called superelasticity, whereby when fabricated as a spring they are able to provide a relatively constant restoring force over the much wider ranges of deflection that they are able to tolerate.

A preferred family of shape memory alloys is nickel/titanium, usually with a nominal atomic composition of 50% nickel and 50% titanium, with small additions of copper, iron, cobalt or chromium, the alloy being subjected to a heat treatment to develop the desired characteristic. One particularly useful alloy in this family comprises 55% nickel and 45% titanium, while another comprises equal amounts of nickel and titanium with 10 atomic % of copper. Other alloys are also known such as copper/zinc/aluminium (usually 15–25 weight% zinc, 6–9 weight % aluminium and the balance copper); copper/zinc/aluminium/manganese; copper/aluminium/nickel (usually 13–14 weight % aluminium, 3–4 weight % nickel and the balance copper); and copper/aluminium/nickel/manganese. At this time the nickel/titanium alloys are preferred in that they have the greatest ductility, more recoverable motion, excellent corrosion resistance comparable to series 300 stainless steels, stable transformation temperatures for shape recovery (memory) effect, high biocompatibility, and the ability to be electrically heated for shape recovery.

The special properties of these alloys make them particularly suitable for the manufacture of spring ligating members for self ligating brackets, and FIGS. 1, 2, 4 and 6 illustrate a bracket of the invention incorporating such a member. Their adoption for this purpose provides unexpected advantages in that, for example, it is possible to make the labial portion 48 of the spring ligating member somewhat longer, which has the result of increasing the energy storage it provides and increasing correspondingly its effectiveness with a particular arch wire, reducing the number of changes that may be required during the course of a procedure. As an example, it has been possible to increase the length of this portion by as much as 0.15 mm–0.25 mm (0.006 in–0.010 in). The values of the elastic modulus of these alloys are much lower than for stainless steels; typical values are for example $11–12\times10^6$ psi. The preferred thickness of the spring ligating members to obtain maximum effectiveness and energy storage is from 0.20 mm (0.008 in) to 0.25 mm (0.010 in), and FIGS. 4 and 6 show a typical size and shape for a ligating spring member of the invention, while FIGS. 3 and 5 show the equivalent shape of a stainless steel ligating spring member of the prior art.

The possibility of using spring material of greater thickness than has been possible hitherto also has unexpected advantages, one of which is that the free edges of the ligating member can easily be well rounded, helping to ensure patient comfort, reducing friction with other elements used in the procedure, and making it less likely to engage in the helical surface grooves of multi-strand arch wires. For example, with existing stainless steel ligating springs it has not been possible to use material thicker than 0.125 mm (0.005 in), since such thicker materials are inherently stressed beyond their elastic limit in mounting the members on their bracket bodies and moving them between slot-open and slot-closed positions. It is also found difficult to round the cut edges of these thin materials, and the best that it has been possible to achieve is a radius of about 0.025 mm (0.001 in), obtained by tumbling; this is to be contrasted with the relatively well rounded edge with radii in the range of from 0.10 mm (0.004 in) to 0.125 mm (0.005 in), and preferably of about 0.1125 mm (0.0045 in) radius, that is possible with the materials employed in the present invention, as clearly shown in FIG. 6.

Another unexpected advantage of the use of these shape memory materials is the possibility of changing the stiffness of the material along the length of the ligature member, in particular arranging that at least the lingual portion 50, whose nominal boundary with the occlusal portion is indicated in FIG. 4 by the reference 65, is stiffer than the remainder of the member. Thus, as the ligature member is moved from the slot closed position by pushing on the free end of the lingual portion, its labial end that is in spring urged engagement with the arch wire is retained by it, bending the occlusal portion of the member to a tighter curve. In the slot closed position the member lingual portion is enclosed in its supporting passage and cannot bend, but as it moves out of this passage, if it is of the same stiffness as the occlusal portion, it will tend to bend with that portion, with the possibility of overstressing, when it may lose at least some of its spring retention capacity. This undesirable effect is reduced by making at least the straight lingual portion as stiff as possible, so that it cannot bend as much with the occlusal portion as it moves out of the constraining slot. At least the labial portion 48 must remain relatively flexible in order for the member to perform its ligating function and to provide the desired active spring force. The portion of the member that is of increased stiffness can extend beyond the lingual portion to include at least part or all of the occlusal portion between the references 65, this reference also being applied to the nominal boundary between the occlusal and labial portions.

The necessary changes in stiffness can be produced by work hardening and subsequent heat treatment of the material. Thus, if in the production of the thin strip the material is subjected to a plastic strain larger than the amount that it will accommodate without deflection, for example of the order of 30%, it becomes much stiffer and harder as the result of work hardening. Normally this subsequently is relieved by subjecting the whole strip to a suitable stress relieving heat treatment. If instead only a part of the strip is subjected to such treatment, while the remainder is shielded, then the shielded part remains stiff while the unshielded part is more flexible. This procedure can be developed further by varying the shielding along the length of the strip, so that the hardness varies correspondingly along its length. With these superelastic materials the degree of stiffness is characterised by the area under the stress strain unloading line, namely the area shown shaded in FIG. 8, this being representative of the amount of elastic energy stored by the spring. The solid unloading line in FIG. 8 is characteristic of a fully stress relieved material, and the smaller area, characteristic of the more flexible material, is shown shaded in solid lines. The broken unloading line is typical for a material that has retained some work hardening and is stiffer, the stored energy and stiffness being represented by the larger area that is shaded in both solid and broken lines. In practice the maximum plastic strain that be applied in a single reducing operation is about 30%, without the ductility becoming too low, and this provides the opportunity for varying the stiffness by up to about 40%.

There are occasions during a procedure in which it is found useful and convenient to employ in addition to a conventional wire or elastic ligature, and with prior art brackets the slot 64 has been used, as described above. As shown in FIGS. 1 and 2 this slot opens to the bracket body at its lingual occlusal junction, and in brackets of the very small body size now employed it becomes more and more difficult to provide a slot of the required size in this location without the possibility of weakening the adjacent part of the body to an undesirable extent. Instead therefore, as shown in FIGS. 9 through 17 and 19 through 24, the bracket body is provided with a mesial distal extending bore 66 disposed between and spaced from the bracket occlusal, lingual and labial surface portions and the arch wire slot occlusal surface portion. The bore is completely surrounded by the body and can be made relatively very large in transverse dimension without compromising the strength of the body, as might be the case if a slot of corresponding size and shape were provided in the same location as the slot 64. Preferably the bore is cylindrical so as to be of circular cross section, although other cross sections can also be used. For example, in a bracket of the size dimensions given above, a cylindrical bore can be of diameter in the range 0.70 mm– 0.90 mm (0.028 in–0.036 in), preferably in the range 0.75 mm and 0.83 mm (0.030 in and 0.033 in).

Figure 10:
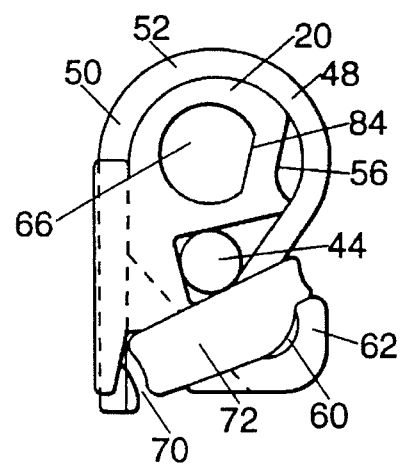
FIG. 10 is a side elevation of the bracket of FIG. 9, illustrating the manner in which an elastomeric loop ligature is used therewith, and showing such a ligature in place.

FIG. 10 illustrates the manner in which at any stage of the procedure an additional elastomeric loop ligature 72 can be placed on the bracket body around the gingival end 54 of the ligating spring member, especially in the event that the orthodontist may suspect that there is the possibility of the arch wire becoming displaced out of the main slot. The secure retention of the ligature on the body is facilitated by the provision of a mesial distal extending slot 70 opening at the junction of the bracket gingival and lingual surface portions; this slot may open to the gingival as shown for example in FIGS. 9–17, 19–21 and and 23, or to the gingival and linguual jointly as shown for example in FIGS. 22 and 23.

Figure 11:
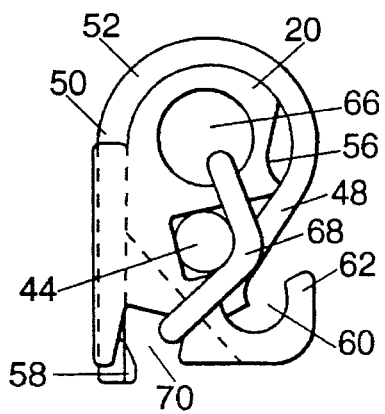
FIG. 11 is a side elevation of the bracket of FIG. 9, illustrating the manner in which an additional wire ligature is used therewith.
Figure 12:
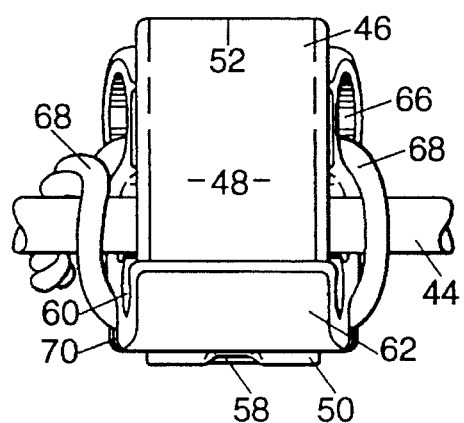
FIG. 12 is an elevation from the labial of the bracket and additional wire ligature of FIG. 11.
Figure 13:
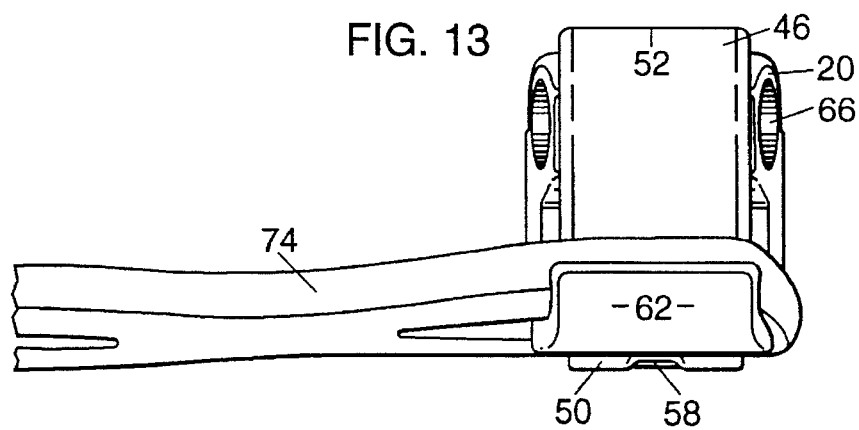
FIG. 13 is an elevation from the labial of the bracket of FIG. 9, showing the way in which an elastomeric traction spring chain is attached thereto.
Figure 14:
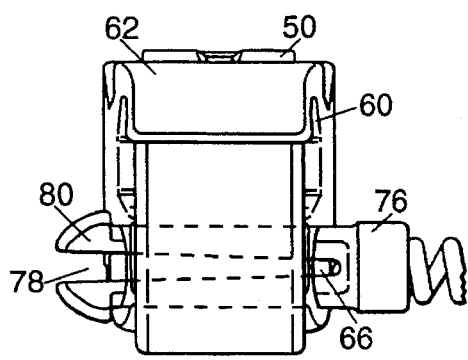
FIGS. 14 and 15 are elevations from the labial of the bracket of FIG. 9, showing respectively an attachment element fully inserted in the bore and positioned to be inserted in the bore.
Figure 15:
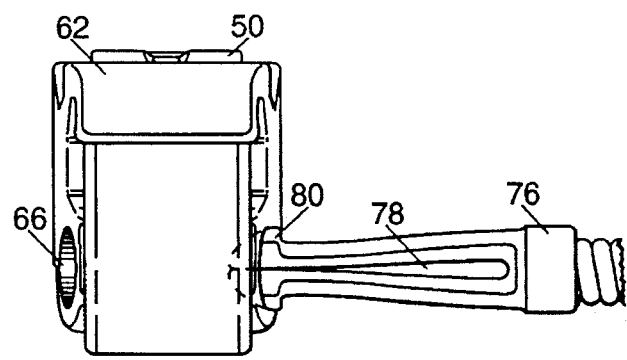

FIGS. 11 and 12 show the manner in which the gingival lingual junction slot 70 and the deep retainer slot 60 cooperate to enable an added wire ligature 68 to be mounted on the bracket whenever required, the central location of the bore 66 permitting the free ends of such a ligature to be twisted neatly and compactly around the wire 44, as illustrated by FIG. 12, to assist in avoiding its engagement with the soft tissue of the patient's mouth. FIG. 13 shows the manner in which these two slots 60 and 70 cooperate to permit the secure retention of the end of an elastomeric chain 74 of loops operating as a traction spring.

This large size bore 66 makes it possible to provide a number of readily added attachments, as illustrated by way of example only by FIGS. 14 through 18. The basic attachment element is an elongated rod-shaped member 76 of generally cylindrical shape which is insertable in the cylindrical bore and retainable therein against at least movement in the mesial distal direction. In these embodiments the body of the attachment member has a longitudinal central slit 78 and radial protrusions 80 at one of its ends, the protrusions being tapered at their free ends and provided with radial shoulders at their junctions with the remainder of the member. The slit permits the radial protrusions to be squeezed together (FIG. 15) when the tapered ends are pushed into the bore entrance, so that the plug can pass through the bore. With the member fully inserted the radial protrusions can move apart for the shoulders to engage the mesial or distal surface portion to retain the plug in the bore against return mesial or distal movement. The attachments are readily removed upon squeezing the protrusions together with a pair of tweezers, or their equivalent.

Figure 16:
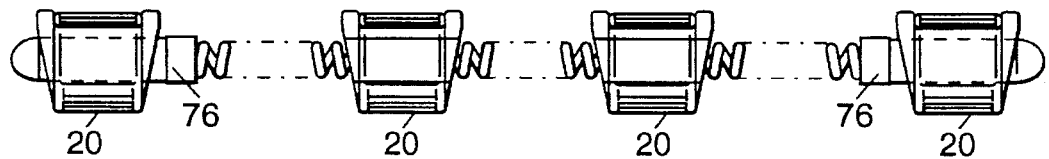
FIGS. 16 and 17 are elevations respectively from the occlusal and the labial of an assembly of the brackets of FIG. 9, as placed on a patient's teeth, and showing the manner in which a helical coil traction spring is used therewith.
Figure 17:
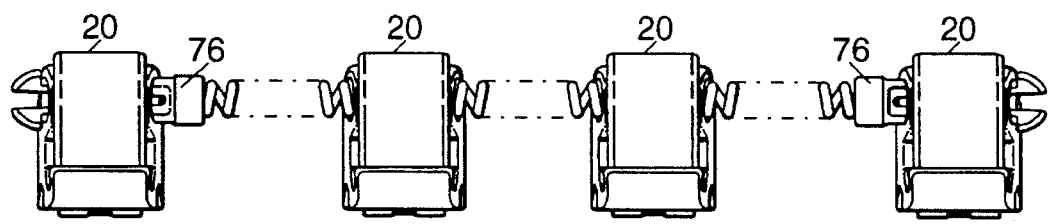

FIGS. 16 and 17 illustrate a situation in an orthodontic procedure in which, by way of example, four brackets 20 are attached to respective teeth (not shown) and it is desired to connect a traction spring between the two outer brackets, but without involving the two inner brackets. This has been difficult with prior art brackets, since the traction spring must lay alongside the two inner brackets, and may foul them, or it might lay against the gum and cause patient discomfort. The brackets are connected by a traction spring of the requisite length and having an attachment member 76 at each of its ends; in this embodiment the traction spring is a helical coil spring. The members 76 and the spring are of such radial dimension that, with the large diameter bore of the invention, they can be threaded through the bores of the two inner brackets, the spring remaining in the bores without appreciable friction and therefore without involving those brackets, and in a manner which holds the spring away from contact with the gum.

Figure 18:
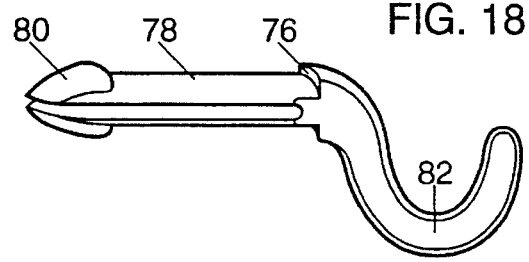
FIG. 18 is a side elevation of an attachment element mountable on the bracket of FIG. 9 and having the form of a hook.

FIG. 18 illustrates an embodiment in which the attachment member 76 has a hook portion 82 formed integrally therewith, so that with the member in place in the bore various other orthodontic elements can be attached to the hook portion. With some attachments it may be desired to not only prevent mesial distal movement of the attachment member, but also rotation about the mesial distal axis. This can be done for example by providing a flat surface 84 in the cylindrical bore wall, so that it is slightly non-circular, as is illustrated by FIG. 10, and by making the plug member body of corresponding non-circular cross-section. Another more preferred way is to provide a groove 86 in the bore wall, as illustrated by FIGS. 19 through 22 and 24, the attachment member body having a radially protruding ridge (not illustrated) that enters the groove to prevent rotation; such embodiments have the advantage that an attachment member without the ridge can rotate freely, so that both rotatable and non-rotatable attachment members can be employed. As indicated, these are examples only of a number of additional attachable auxiliaries that can be provided, others examples being lip bumpers and headgear.

Figure 19:
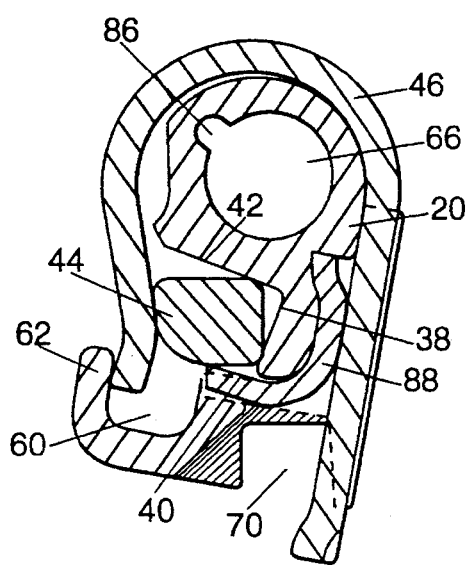
FIG. 19 is an occlusal gingival cross section through a bracket which is further embodiment of the invention, in which an auxiliary or additional spring provides the gingival wall of the arch wire slot, and showing a typical position of an arch wire in the slot at the beginning of an orthodontic procedure.
Figure 20:
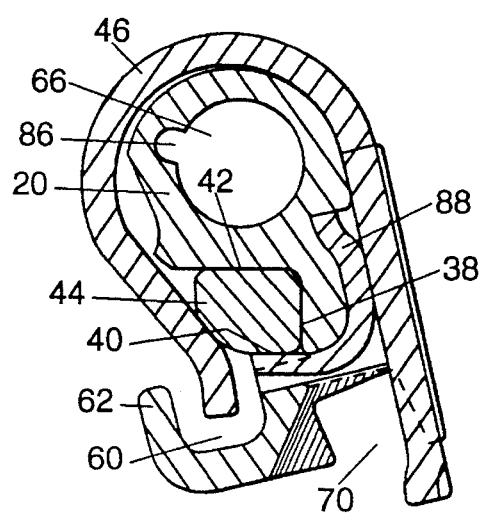
FIG. 20 is a cross section similar to FIG. 19 and showing the position of the arch wire in the slot at the end of the procedure.
Figure 21:
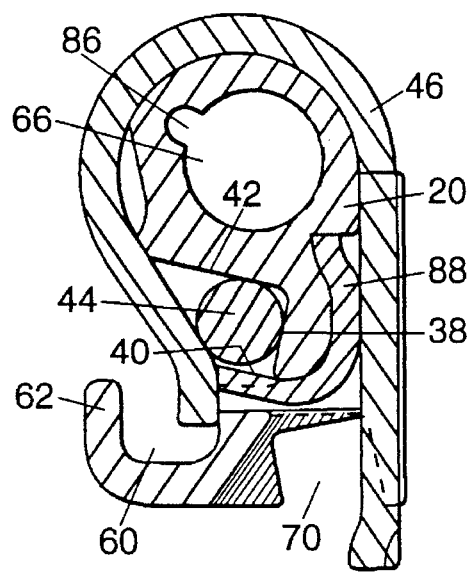
FIG. 21 is a cross section similar to FIG. 19 and showing the use of the bracket in cooperation with an arch wire of round cross section.

FIGS. 19 through 21 illustrate an embodiment of the invention in which, in order to facilitate the cooperative action between the arch wire and arch wire slot surfaces, the slot gingival surface 40 is provided by an additional spring member 88 having its lingual end retained between the body and the ligating member lingual portion 50, while its labial end is free to move gingivally, if so engaged by an arch wire in the slot, its spring force adding to that already provided by the spring ligating member 46. FIG. 19 illustrates the situation at the start of a typical procedure, using my part rectangular cross section arch wire described above, where the arch wire and the bracket are displaced from their optimum relation, so that the labial end of the additional spring member 88 is displaced gingivally, and the labial portion of the ligating spring member 46 is displaced labially into contact with the retaining wall 62. The slot gingival and occlusal walls are no longer completely parallel and both springs cooperate in urging the bracket and wire toward their optimum relation, as shown in FIG. 20, in which these walls are parallel. In view of the very small displacements that such a spring is likely to be subjected to, usually not more than 0.05 mm (0.002 in), it can be of a stainless steel. It may be preferred however to use the thicker shape memory alloy materials, even though at present they are more expensive than stainless steel.

The use of a shape memory alloy material results in a self-ligating bracket with an unexpected very useful facility. To achieve this the spring is preset to an initial shape such that when first installed its labial end is displaced to the maximum in the gingival direction, as indicated in broken lines in FIGS. 19 and 20, while its "memory" shape is the optimum shape illustrated by FIG. 20. A spring of this initial shape effectively initially forms an arch wire slot that is enlarged in the gingival direction, making it correspondingly easier for the wire to be inserted in the slot when there is substantial misalignment between them. The initial movement of the wire and bracket toward the optimum relation is produced only by the interaction between the ligating spring member 46 and the arch wire 44. If at any time the decision is made that the additional effect of the spring 88 is needed, the spring is heated to its transformation temperature, for example by application of a heated cauterising tool to it through the slot 70, whereupon it returns to its memory shape and becomes operative. FIG. 21 illustrates the use of the bracket of the invention with a round wire which fits into the slot formed when the two springs are both in their optimum "fully home" positions.

Figure 22:
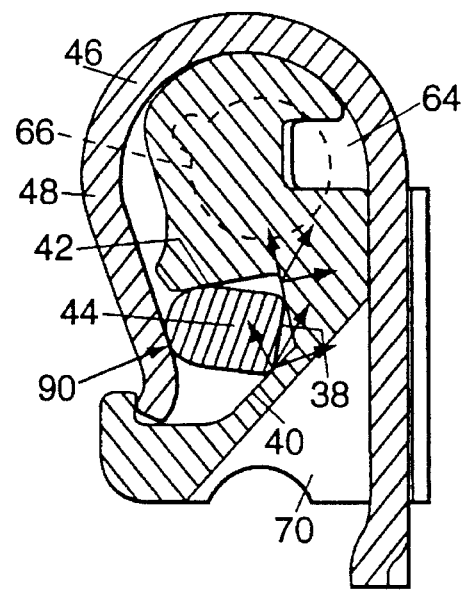
FIG. 22 is an occlusal gingival cross section through a bracket which is further embodiment of the invention, and showing a typical position of an arch wire in the slot at the beginning of an orthodontic procedure.
Figure 23:
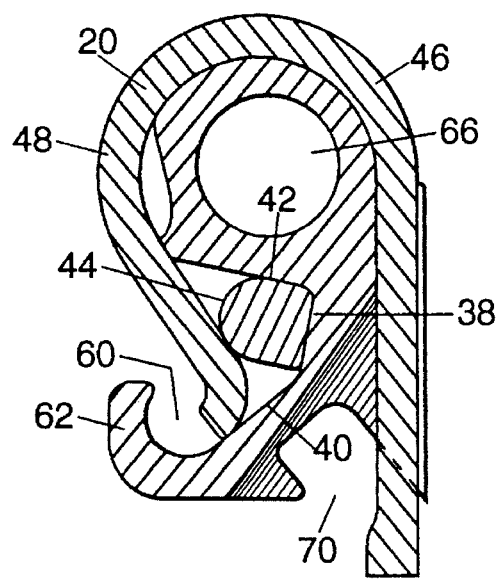
FIG. 23 is a cross section similar to FIG. 22, through a bracket which is further embodiment of the invention, and showing a typical position of an arch wire in the slot at the end of an orthodontic procedure.
Figure 24:
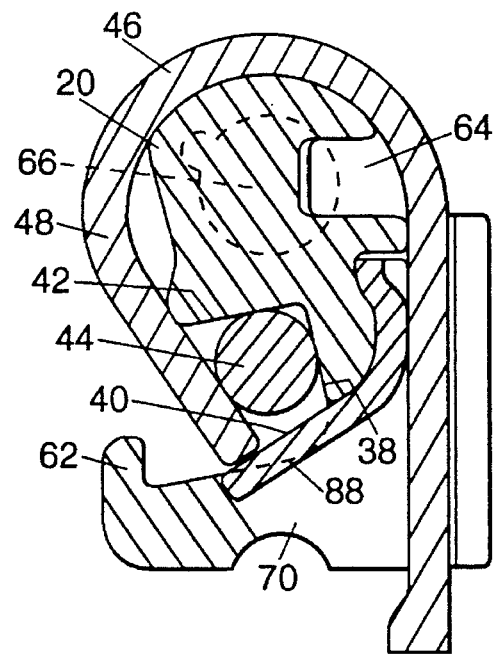
FIG. 24 is a cross section similar to FIG. 22 and showing a further embodiment in which an auxiliary or additional spring provides the gingival wall of the arch wire slot.

In the prior art brackets described above in which the arch wire slot is rectangular the two junctions between the slot occlusal and lingual walls, and between the slot gingival and lingual walls, are both right angle junctions. As described, such a slot to be effective must be of dimension such that the wire fits within it without appreciable play, and this makes it difficult to insert the wire at the start of a procedure, especially if there is much misalignment to be accommodated. The use of the second auxiliary spring 88 makes such insertion easier by effectively temporarily increasing the size of the slot opening. FIGS. 22 through 24 illustrate embodiments in which the arch wire slots are permanently of larger than rectangular cross section in order to obtain this effect. Thus, in these brackets the gingival and occlusal walls of the slot are no longer parallel, and instead the gingival wall 40 is inclined downward so that the slot tapers inward in the lingual direction. More specifically, the slot lingual and occlusal surface portions 38 and 42 still meet at a common junction at least approximately at a right angle to one another, but the lingual and gingival surface portions 38 and 40 instead meet at a common junction at an angle to one another more than 90 degrees, so that the gingival surface portion 40 is inclined downward gingivally and labially. This angle may be from 120 to 150 degrees, and preferably is about 135 degrees. As described above, such an enlarged slot makes it very much easier for an arch wire to be introduced into the slot and the ligating spring to be closed on it than has been possible with rectangular slots. Thus, the wire previously could only be inserted by rotating it until it was in the attitude in which it could be fitted into the rectangular cross section slot, but clearly this is not necessary with the slot cross section of the invention.

FIG. 22 illustrates a typical example of the cooperative action between the bracket, the arch wire, and the ligating spring member when a relatively unrotated arch wire 44 has been inserted in the slot. The force exerted by the ligating spring member on the wire via its labial portion 48 is indicated by the arrow 90, while the corresponding forces and their resultants produced upon engagement of the wire junctions with the slot lingual and gingival surface portions are indicted by respective sets of smaller arrows; it will be seen that they result in a couple applied to the wire, rotating it about a mesial-distal axis anti-clockwise as seen in FIG. 22, this rotation being facilitated by the ramp-like engagement between the junctions of the wire surfaces and the respective slot faces which they engage. This couple will continue to be operative in this manner until the relative rotation between the wire and the bracket has moved the latter and its attached tooth to the position shown in FIG. 23, in which the occlusal and lingual faces are in butting engagement with the slot occlusal and lingual faces respectively, and with right angle junction between the wire occlusal and lingual faces is in butting engagement with the corresponding junction between the slot occlusal and lingual faces.

For the orthodontist this provides a number of interesting alternatives that give increased flexibility in the organization of a procedure, in that the requirement to provide a rotational spring force can be shared more easily between the arch wire and the ligating spring member. For example, with prior art procedures with badly misplaced teeth, after the maximum initial correction has been obtained with round arch wires, a thin and relatively springy rectangular arch wire must first be used in order to be able to insert it without damage and overstressing of both the teeth and the brackets into the bracket slots, followed by progressively stiffer wires. With these new brackets it is possible to move more quickly from a very springy wire to a very stiff wire, with the possibility of eliminating the need for a wire or wires of intermediate stiffness, since it is now possible to insert even a very stiff wire into the bigger slots, the necessary rotational correcting force now being provided predominantly by the ligating spring.

A very unexpected advantage of the new slot cross section is that the expression of the desired relative rotational position between the arch wire and the bracket is no longer dependent upon very accurate correlation between the relative dimensions of the wire and the slots. Thus, during manufacture of the wire and the bracket at an economic price there will always be minor variances in dimensions corresponding to the usual inevitable manufacturing tolerances. It must always be possible to insert the wire relatively easily into the slot, and this dictates that there will always be some minimum clearance between them; in practice owing to these tolerances the clearance will frequently be larger than the minimum, and will result in the possibility of rotation of the bracket from the optimum position of a few degrees, when the wire can no longer rotate the bracket. Such a clearance is easily visible in the lack of rotational alignment of the affected teeth and requires further correction. With the brackets of the invention the expression of the rotational position is set by the surface to surface engagement of the respective occlusal and lingual surface portions, and all that is required is to ensure that the junctions between the surface portions are accurately at the same angles to one another; with modern manufacturing techniques this can be done to within a few minutes of arc. It will be seen that the angles theoretically do not need to be right angles as long as they are the same, but in practice a right angle will be used so that the brackets can also be used with standard rectangular cross section wires.

The stainless steel ligating spring members previously used can also be used with these new brackets, although the greater tolerance for displacement of the labial portion of the ligating spring member provided by the use of shape memory alloys is advantageous and preferably such ligating spring members are used. FIG. 24 illustrates a yet further development of these brackets in which the downwardly inclined slot gingival surface is provided by an additional or auxiliary spring 88, which again can be of stainless steel or preferably of shape memory alloy to obtain the advantageous effect described above. It will be noted that any of the brackets of FIGS. 22 through 24 can be provided either with a slot 64, or with a large bore 66 (indicated in broken lines in FIGS. 22 and 24), and can be provided with a deep slot 60 as illustrated by FIG. 23.

I claim:

1. An orthodontic bracket comprising:
   a bracket body having labial, lingual, gingival, occlusal, mesial and distal surface portions, and having a mesial distal extending arch wire slot opening to the labial surface portion; and
   a generally U-shaped ligating spring member of thin resilient material having labial and lingual portions in embracing sliding engagement with corresponding labial and lingual surface portions of the body, the ligating spring member being movable on the body between two positions in which the slot labial opening is respectively open and closed;
   wherein the ligating spring member is of a superelastic shape recovery metal alloy.

2. A bracket as claimed in claim 1, wherein the thickness of the ligating spring member is from 0.20 mm (0.008 in) to 0.25 mm (0.010 in).

3. A bracket as claimed in claim 1, wherein the edges of the ligating spring member are rounded to a respective radius of from 0.10 mm (0.004 in) to 0.125 mm (0.005 in).

4. A bracket as claimed in claim 1, wherein at least the lingual portion of the ligating spring member is of greater stiffness than the remainder of the member.

5. A bracket as claimed in claim 4, wherein the lingual portion and at least a part of the occlusal portion of the ligating spring member are of greater stiffness than the remainder of the member.

6. A bracket as claimed in claim 1, wherein the arch wire slot gingival surface portion is provided by an additional spring member having its lingual end retained by the bracket body and having its labial end free to move gingivally by engagement with an arch wire in the slot.

7. A bracket as claimed in claim 6, wherein the additional spring member is of superelastic shape recovery metal alloy.

8. A bracket as claimed in claim 7, wherein the additional spring member is of preset shape such that the slot lingual and gingival surface portions meet at a common junction at an angle to one another of more than 90 degrees, and wherein the additional spring member has been pretreated so that upon heating above a transition temperature its preset shape is changed to a memory shape with which the lingual and gingival surface portions meet at a common junction at an angle of 90 degrees.

9. A bracket as claimed in claim 1, and comprising a mesial distal extending bore disposed between and spaced from the bracket occlusal, lingual and labial surface portions and the arch wire slot occlusal surface portion.

10. A bracket as claimed in claim 9, in combination with an attachment member insertable in the bore and retainable therein against at least movement in the mesial distal direction.

11. A bracket as claimed in claim 10, wherein the attachment member has a longitudinal central slit and radial protrusions at one of its ends, the slit permitting the radial protrusions to move together to permit the attachment member to be inserted into and pass through the bore, the radial protrusions moving apart after passage of the member through the bore and retaining it in the bore against return mesial distal movement.

12. A bracket as claimed in claim 10, wherein the attachment member is attached to one end of an orthodontic element of transverse dimension small enough for it to pass through the bores of adjacent brackets.

13. A bracket as claimed in claim 12, wherein the orthodontic element is a traction spring.

14. A bracket as claimed in claim 10, wherein the attachment member has at one end a hook member for reception and retention of a ligature member.

15. A bracket as claimed in claim 1, wherein the arch wire slot has lingual, gingival and occlusal surface portions, wherein the lingual and occlusal surface portions meet at a common junction at least approximately at a right angle to one another, and wherein the lingual and gingival surface portions meet at a common junction at a greater angle to one another of from 120 to 150 degrees.

16. An orthodontic bracket comprising:
    a bracket body having labial, lingual, gingival, occlusal, mesial and distal surface portions, and having a mesial distal extending arch wire slot opening to the labial surface portion; and
    a generally U-shaped ligating spring member of thin resilient material having labial and lingual portions in embracing sliding engagement with corresponding labial and lingual surface portions of the body, the ligating spring member being movable on the body between two positions in which the slot labial opening is respectively open and closed; and
    wherein the arch wire slot gingival surface portion is provided by an additional spring member having its lingual end retained by the bracket body and having its labial end free to move gingivally by engagement with an arch wire in the slot.

17. A bracket as claimed in claim 16, wherein the additional spring member is of superelastic shape recovery metal alloy.

18. A bracket as claimed in claim 17, wherein the additional spring member is of preset shape such that the slot lingual and gingival surface portions meet at a common junction at an angle to one another of more than 90 degrees, and wherein the additional spring member has been pretreated so that upon heating above a transition temperature its preset shape is changed to a memory shape with which the lingual and gingival surface portions meet at a common junction at an angle of 90 degrees.

19. A bracket as claimed in claim 16, wherein the arch wire slot has lingual, gingival and occlusal surface portions, the lingual and occlusal surface portions meeting at a common junction at least approximately at a right angle to one another, and wherein the lingual and gingival surface portions meet at a common junction at an angle to one another of from 120 to 150 degrees.

20. An orthodontic bracket comprising:

a bracket body having labial, lingual, gingival, occlusal, mesial and distal surface portions, and having a mesial distal extending arch wire slot opening to the labial surface portion, the slot having lingual, gingival and occlusal surface portions; and a generally U-shaped ligating spring member of thin resilient material having labial and lingual portions in embracing sliding engagement with corresponding labial and lingual surface portions of the body, the member being movable on the body between two positions in which the slot labial opening is respectively open and closed;

the bracket also comprising a mesial distal extending bore disposed between and spaced from the bracket occlusal, lingual and labial surface portions and the arch wire slot occlusal surface portion.

21. A bracket as claimed in claim 20, wherein the bore is of diameter in the range 0.70 mm–0.90 mm (0.028 in–0.036 in).

22. A bracket as claimed in claim 20, in combination with an attachment member insertable in the mesial distal extending bore and retainable therein against at least movement in the mesial distal direction.

23. A bracket as claimed in claim 22, wherein the attachment member has a longitudinal central slit and radial protrusions at one of its ends, the slit permitting the radial protrusions to move together to permit the attachment member to be inserted into and pass through the bore, the radial protrusions moving apart after passage of the member through the bore and retaining it in the bore against return mesial distal movement.

24. A bracket as claimed in claim 20, in combination with an attachment member insertable in the mesial distal extending bore and retainable therein against movement in the mesial distal direction and rotation about a mesial distal axis.

25. A bracket as claimed in claim 24, wherein the bore is of non-circular transverse cross section and the attachment member is of corresponding non-circular transverse cross section to prevent rotation of the member about a mesial distal axis when inserted in the bore.

26. A bracket as claimed in claim 24, wherein the bore has a radially extending groove in its wall and the attachment member has a cooperating radial projection that engages in the groove to prevent rotation of the member about a mesial distal axis when inserted in the bore.

27. A bracket as claimed in claim 24, wherein the attachment member is attached to one end of an orthodontic element of transverse dimension small enough for it to pass through the bores of adjacent brackets.

28. A bracket as claimed in claim 27, wherein the orthodontic element is a traction spring.

29. A bracket as claimed in claim 24, wherein the attachment member has at one end a hook member for reception and retention of a ligature member.

30. A bracket as claimed in claim 20, and comprising a mesial distal extending slot disposed at the junction of the bracket body gingival and lingual surface portions and opening to the bracket body gingival surface portion.

* * * * *